United States Patent [19]

Cameron et al.

[11] Patent Number: 5,113,032

[45] Date of Patent: May 12, 1992

[54] PROCESS FOR PRODUCING OLEFINS FROM NATURAL GAS

[75] Inventors: Charles Cameron, Paris; Hubert Mimoun, Rueil-Malmaison; Alain Robine, Rueil-Malmaison; Serge Bonnaudet, Rueil-Malmaison; Patrick Chaumette, Bougival; Quang Dang Vu, Neuilly, all of France

[73] Assignee: Institut Francais Du Petrole, Rueil-Malmaison, France

[21] Appl. No.: 461,874

[22] Filed: Jan. 8, 1990

[30] Foreign Application Priority Data

Jan. 6, 1989 [FR] France ................ 89 00188

[51] Int. Cl.$^5$ ................................ C07C 2/00
[52] U.S. Cl. .................... 585/500; 585/601; 585/654; 585/656; 585/658; 585/661; 585/700; 585/943
[58] Field of Search ............ 585/314, 500, 943

[56] References Cited

U.S. PATENT DOCUMENTS

| | | | |
|---|---|---|---|
| 2,011,199 | 8/1935 | Pelc | 585/943 |
| 2,022,279 | 11/1935 | Feiler | 585/943 |
| 2,027,460 | 1/1936 | Youker | 585/943 |
| 2,028,014 | 1/1937 | Reinecke | 585/943 |
| 2,080,767 | 5/1937 | Dreyfus | 585/943 |
| 2,221,658 | 11/1940 | Waterman et al. | 585/943 |
| 2,318,626 | 2/1945 | Pier | 585/943 |
| 4,929,787 | 5/1990 | Cameron et al. | 585/500 |
| 4,413,153 | 11/1983 | Garwood et al. | 585/314 |
| 4,533,780 | 8/1985 | Maffia | 585/500 |
| 4,547,607 | 10/1985 | Jones et al. | 585/943 |
| 4,724,272 | 2/1988 | Raniere et al. | 585/943 |
| 4,727,212 | 2/1988 | Gaffney | 585/500 |
| 4,751,336 | 6/1988 | Jezl et al. | 585/500 |
| 4,814,534 | 3/1989 | Devries et al. | 585/500 |
| 4,814,538 | 3/1989 | Devries et al. | 585/500 |
| 4,879,427 | 11/1989 | Sofranky | 585/943 |
| 4,939,310 | 7/1990 | Wade | 585/943 |
| 5,025,108 | 6/1991 | Cameron et al. | 585/500 |

Primary Examiner—Helane Myers
Attorney, Agent, or Firm—Millen, White & Zelano

[57] ABSTRACT

Process for producing olefins from natural gas, the natural gas (2) is mainly fractionated (1) into methane (3) and higher hydrocarbons (4), the latter being then mainly fractionated (17, 20) into propane (9) and ethane (7). The methane (3), admixed with oxygen (6), passes through an oxidation reactor (5), receives the ethane (7) and the obtained mixture passes through a pyrolysis reactor (8). The effluent coming out of reactor (8) receives the propane (9) and the obtained mixture passes through a pyrolysis reactor (10). A hydrocarbon flow comprising olefins (12), more particularly ethylene and propene, is recovered.

23 Claims, 1 Drawing Sheet

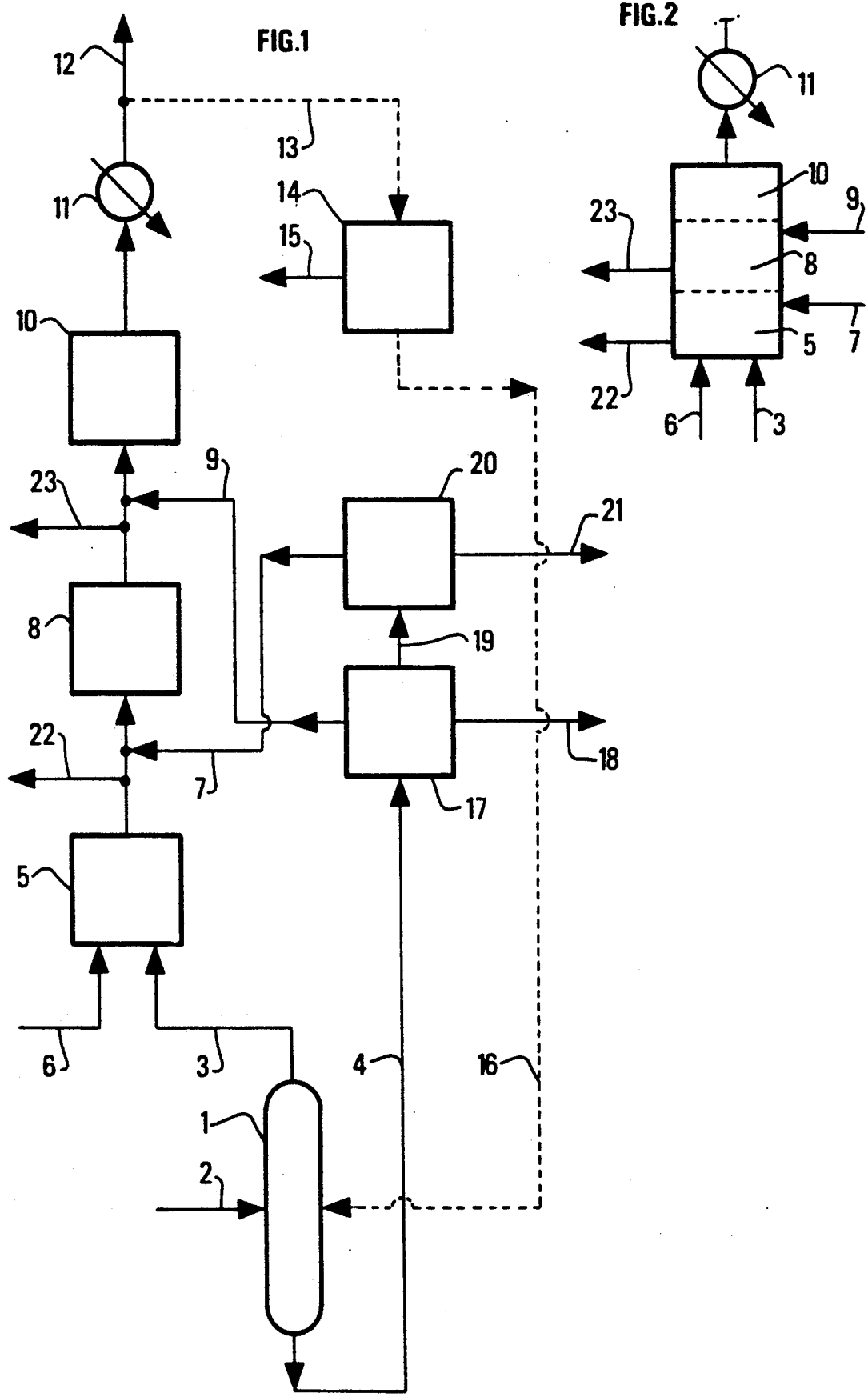

PROCESS FOR PRODUCING OLEFINS FROM NATURAL GAS

BACKGROUND OF THE INVENTION

The present invention relates to a process for producing olefins from natural gas.

Natural gas is an abundant fossil raw material which is essentially composed of methane, the present proven reserves of which, about $10^{14}$ m$^{3''}$, represent about 50 years of world consumption. Gas fields often contain considerable amounts of ethane, propane, other higher alkanes, as well as other constituents such as $H_2O$, $CO_2$, $N_2$, $H_2S$, and He. Most of the propane and of the other higher alkanes associated with natural gas are liquefied and called LPG (liquefied petroleum gas). In helium-rich fields (generally more than 0.3% by volume), the helium is separated because of its high commercial value. The hydrogen sulfide is also separated because of its corrosive character, as is the water because of the forming of hydrates which are harmful to the transportation of natural gas. The obtained natural gas is then called non condensed gas, and it mainly contains (for example 55-99% by volume) methane as well as ethane, generally propane and possibly low amounts of nitrogen and/or carbon dioxide.

Most of the natural gas is used for domestic and industrial heating; however, there are some processes for converting natural gas into higher hydrocarbons.

The direct conversion of natural gas into ethylene would be a highly desirable objective. since ethylene can serve as a raw material for numerous syntheses of important products. Both the pyrolysis and the catalytic pyrolysis of methane are both processes which aim to achieve this objective. However, these are very endothermic processes which require considerable amount of energy. Besides, these two processes produce large amounts of an desired coke.

The pyrolysis of ethane is also a well-known process which is very endothermic and thus is a large energy consumer. However, as the pyrolysis of ethane is carried out at lower temperatures than that of methane, it is not possible to simultaneously convert these two compounds. Thus, when the process is operated at the conversion temperature of ethane, the methane which is present in the ethane-containing charge comes out of the reactor essentially unchanged.

To produce ethylene and other hydrocarbons, the oxidizing coupling of methane, either in the sequential or in the simultaneous mode, has been suggested.

The reaction of the oxidizing coupling in the sequential mode consists of the oxidation of the methane by a reducing agent, followed by the re-oxidation of this agent, separately, by the oxygen in the air. Several U.S. patents (for example U.S. Pat. Nos. 4,499,323; 4,523,049; 4,547,611; 4,567,307) have mentioned the use of numerous metal oxides, mainly Mn, Ce, Br, Sn, In, Ge, Rb, Sb, Bi, Tb, as reducing agents for this reaction.

The reaction of the oxidizing coupling in the simultaneous mode (scavenging of a mixture of methane and oxygen on a contact mass) can be written qualitatively:

other hydrocarbons + CO + $CO_2$ + $H_2$ + $H_2O$

The use of rare-earth oxides, of alkaline and alkaline-earth oxides, and of titanium, zirconium, hafnium and zinc oxides, either alone or mixed, as catalysts for the reaction of the oxidizing coupling of methane in the simultaneous mode has been mentioned in several patents (for example European patents EP 210,383 A2; EP 189,079 A1; EP 206,044 A1 and world patent WO 86 07351).

It has to be noticed that the previous processes works concerning the oxidizing coupling of methane have led to the forming of low ethylene to ethane ratios, generally ranging from about 0.8 to 1.2 for $C_2+$ product selectivities higher than about 65%. Such low ethylene to ethane ratios require the separation of ethane from ethylene and the costly pyrolysis of ethane into ethylene. Besides, the previous processes for the oxidizing coupling of methane have not taken into account the other major constituents of natural gas such as ethane, propane and other saturated hydrocarbons. The processes for the oxidizing coupling of methane described above are little applicability for the selective conversion of natural gas into olefins because of the presence of significant amounts of light hydrocarbons (such as ethane and propane) in natural gas. The relative oxidation velocities of light alkanes under the conditions of the oxidizing coupling of methane are about 15 to 100 times higher than those of the oxidation of methane, that is to say that the light hydrocarbons are converted into ethylene and carbon oxides before the methane begins to react. Thus, the previous processes cannot be efficiently applied to natural gas.

Considering the sometimes appreciable presence of propane, possibly of other light alkanes in natural gas and possibly of light hydrocarbons from other units located for example close to the natural gas oxipyrolysis unit, it is very advantageous to upgrade, besides the methane and the ethane, the propane and possibly other higher alkanes.

OBJECT OF THE INVENTION

Thus, one object of the present invention is to provide a method for producing olefins, mainly ethylene and propene, with a high yield, from natural gas.

Another object of the present invention is to provide a method for the dehydrogenation of the alkanes coming out of the methane oxidation reactor without requiring an independent pyrolysis reactor.

DESCRIPTION OF THE INVENTION

These objectives are reached by the present process of oxipyrolysis of natural gas which comprises the following stages:

(1) separation of the natural gas into two fractions: a first gas fraction enriched with methane (which is preferably substantially free from ethane, propane and other hydrocarbons associated with natural gas) and a second gas fraction enriched with hydrocarbons higher than methane (particularly ethane and propane, and which may or not also contain non hydrocarbon gases);

(2) selective oxidation of the first methane-containing gas fraction by molecular oxygen, in the presence of a contact mass, to form an effluent containing $C_2$ hydrocarbons and water as main products;

(3) separation of the second gas fraction enriched with hydrocarbons higher than methane into two new fractions: a first propane-enriched gas fraction and a second ethane-enriched gas fraction;

(4) addition of the second ethane-enriched gas fraction from stage (3), alone or in the presence of a gas enriched with ethane that does not stem from natural gas, to the effluent from the selective oxidation reaction of methane from stage (2), in a place where at least about 80% (preferably at least about 95%) by volume of the molecular oxygen introduced in stage (2) have been consumed:

(5) pyrolysis of the mixture of said effluent and said second gas fraction enriched with ethane from stage (3):

(6) addition of the first propane-enriched gas fraction from stage (3), alone or in the presence of a gas enriched with propane that does not stem from natural gas, to the pyrolysis effluent from stage (5), in a place where said pyrolysis effluent from stage (5) has an olefins/$C_2+$ alkanes molar ratio of at least 0.5 ; and (7) pyrolysis of the mixture from stage (6), in order to produce an olefin-rich gaseous mixture.

The process of oxipyrolysis of natural gas according to the present invention has the following main advantages:

a) the heat released during the selective oxidation reaction of the methane (approximately 250 kJ per mole of methane having reacted) is immediately used for the pyrolysis of the effluent alkanes and of the other added alkanes;

b) the sequential addition of ethane, then of propane allows to take a better advantage of this heat release;

c) appropriate olefins/alkanes ratios can be obtained by controlling the residence times in pyrolysis stages (5) and (7) and the temperature of the gaseous effluent which immediately results from the selective oxidation of the methane:

d) the effluent from the selective oxidation reaction of the methane can serve as a dehydrogenation diluent for a pyrolysis reaction of ethane and other saturated hydrocarbons which can be introduced after the initial oxidation reaction:

e) the necessity of separately converting ethane into ethylene and propane into propene by a conventional pyrolysis process is eliminated: and f) the process allows one to treat the total natural gas and not only the methane contained in the natural gas; particularly the addition of propane, and possibly of other higher alkanes, after that of ethane, allows one to better upgrade the $C_3+$ alkanes.

In relation to a process where the addition of ethane and of propane to the effluent of the methane oxidation reaction would be simultaneous, the process of the invention particularly allows one to avoid a substantial conversion of the propane into propene, followed by a degradation of the propene before obtaining a high conversion rate of ethane into ethylene.

Concerning the contact mass (catalyst) for the selective oxidation reaction of methane into higher hydrocarbons [stage (2) of the process according to the invention], although it is possible to use any well-known contact mass to do so, it is preferred to utilize a contact mass which:

a) can operate at the normal conditions of the oxidizing coupling, for example at temperatures ranging from about 650° to about 1.200° C. preferably from about 650° to about 950° C.

b) produces $C_2+$ products with a selectivity of at least about 65% for a methane conversion rate of about 15%, and c) maintains its activity and its selectivity for numerous operating hours.

The contact masses which correspond to the conditions above and the use of which is thus preferred are those which generally contain oxides and/or carbonates of alkaline metals (such as lithium, sodium, potassium, rubidium and cesium), of alkaline-earth metals (such as beryllium, magnesium, calcium, strontium and barium) and of rare-earth metals (such as yttrium, lanthanum, praseodymium, neodymium, samarium, gadolinium, terbium, dysprosium, holmium, erbium, thulium, ytterbium, europium and lutetium), either alone (as in the case of rare-earths and alkaline-earths), or mixed (as in the case of alkaline-earth metals doped with alkali metals and of rare-earth metals doped with alkaline and/or alkali-earth metals). Other contact masses which correspond to the conditions above are chose that contain oxides and/or carbonates of titanium, zirconium, hafnium, manganese, cerium, tin, indium, germanium, lead, antimony, zinc and bismuth, preferably with one or several oxides and/or carbonates of alkaline, alkaline-earth and rare-earth metals and silica. The contact masses cited above are efficient alone or doped with halogenides, phosphorus or sulfur oxides.

It is also interesting that the contact masses for the selective oxidation of methane:

(a) be effective for very short contact times, generally less than about 300 milliseconds, (b) be able to consume at least about 80% (preferably at least about 95%) by volume of the molecular oxygen in the charge during very short contact times.

The contact masses which are particularly interesting are the following:

(a) Contact masses containing alkaline-earth and rare-earth compounds and approximately corresponding to the following formula:

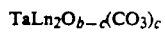

$$T_aLn_2O_{b-c}(CO_3)_c$$

where T represents one or several alkaline-earth metals such as beryllium, magnesium, calcium, strontium and barium. Ln represents one or several rare-earth metals such as yttrium. lanthanum, cerium, praseodymium, neodymium, samarium, europium, gadolinium, terbium, dysprosium, holmium, erbium, thulium, ytterbium and lutetium, a=0.001 to 1.000; b=3+a; c=0.1 to b; the preferable rare-earth metals are lanthanum, neodymium and samarium, alone or mixed; the preferred rare-earth metal is lanthanum.

(b) Contact masses containing alkaline-earth, rarearth and group IVA compounds and approximately corresponding to the following formula:

$$T_aM_dLn_2O_{e-f}(CO_3)_f$$

where T represents one or several alkaline-earth metals, M represents one or several metals from group IV A such as titanium, zirconium and hafnium, Ln represents one or several rare-earth metals, a=0.001 to 1,000; d=0.001 to 2; e=3+a+2d−z; f=0.1 to e; z=0 to 0.5 d; in this formula, z represents a value from 0 to 0.5 d thus, z is equal to 0 when the oxidation state of all the metals from group IV A is +4, 0.5 d when the oxidation state of these metals is +3, and ranges from 0 to 0.5 d when there is a mixture of the oxidation states +3 and +4 of these metals; the preferred rare-earth metals are lanthanum, neodymium and samarium, and more particularly lanthanum.

Contact masses (a) and (b) are nevertheless not limited to the formulas above. In fact, the beneficial effect of the presence of rare-earth and alkaline-earth metals and possibly of metals from group IV A appears whatever the form under which these metals are present, although the oxide and/or carbonate form is preferred.

(c) Contact masses containing two or more alkaline-earth metals and approximately corresponding to the following formula:

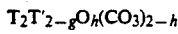

$$T_2T'_{2-g}O_h(CO_3)_{2-h}$$

where T represents one or several alkaline-earth metals that are different from T', such as beryllium, magnesium, calcium, strontium and barium, T' represents an alkaline-earth metal known for forming carbonates that are stable at high temperature, such as calcium, strontium and baryum, $g=0.1$ to $1.8$, $h=0$ to $2$; the preferable T' alkaline-earth metals are strontium and baryum.

Contact masses (c) are nevertheless not limited to the formula above. In fact, the beneficial effect of the presence of at least two alkaline-earth metals (or at least one component such as calcium, strontium or, barium appears whatever the form under which these metals are present, although the carbonate or the oxide and carbonate form is preferred.

The gas fraction subjected to the oxidation (stage (2) of the process according to the invention) can be used without a diluent or diluted by inert gases such as nitrogen, carbon dioxide or steam. For security reasons and in order to avoid too high a temperature rise, which would be harmful to the selectivity of the operation, the oxygen content in the methane can generally not exceed 40% by mole; it can thus range from about 0.1 to 40% by mole, preferably from about 5 to 25% by mole.

The temperature of the oxipyrolysis reaction (stages (2), (5) and (7) of the process according to the invention) generally ranges from about 650 to about 1,200° C., preferably from about 650 to about 950° C.

The total pressure (stages (2), (5) and (7)) can for example range from about 1 to about 100 bars, and especially from about 1 to about 20 bars. The contact time of the oxidizing coupling of methane (that is the time necessary for achieving the consumption of at least about 80% of the molecular oxygen in the charge) usually ranges from $10^{-6}$ to 1 second, preferably from $10^{-6}$ to $10^{-1}$ second. The total residence time in both pyrolysis section (stages (5) and (7) of the process according to the invention) preferably ranges from about $10^{-5}$ to 10 seconds, and especially from about $10^{-3}$ to 2 seconds.

The selective oxidation of the gas fraction containing methane (stage (2) of the process according to the invention) can be implemented in any reactor type, particularly in a fixed bed, an ebuilated bed, a circulating bed or a fluidized bed reactor, preferably in a fixed bed reactor.

The following non limitative examples represent embodiments which can be used for performing the oxipyrolysis of natural gas according to the invention, with the stepped addition of $C_2+$ saturated hydrocarbons after the stage of selective oxidation of the methane, and are illustrated by FIGS. 1 and 2.

BRIEF DESCRIPTION OF THE DRAWINGS

FIG. 1 is a block flow sheet of a preferred comprehensive embodiment of the invention, and FIG. 2 illustrates an alternative system, wherein instead of distinct reactors, there is a single reactor having three successive reaction zones.

DETAILED DESCRIPTION

A natural gas flow (2), preferably purified (having for example been subjected to the usual dehydration, desulfurization and decarbonatation treatments), is fractionated in separator (1) into a gas fraction rich in methane (3) and a gas fraction rich in hydrocarbons higher than methane (4). The flow of methane-rich gas fraction (3) is pre-heated, either alone or in the presence of steam, at a temperature which does not generally exceed about 650° C., then it is admixed with a gas rich in molecular oxygen (6) before being contacted with the fixed bed in reactor (5). The contact mass (which can be present in the fixed bed in the form of a powder, granules, extrudates, pellets or supported on oxides and/or carbonates of alkaline-earth and/or rare-earth metals, on zircon, silica, alumina, quartz or on monoliths such as cordierite, mullite or alpha alumina) is heated up, by the exothermicity of the oxidation reaction, at a temperature generally ranging from about 650° to about 1,200° C. The temperature of the contact mass is a function of the initial temperature of the gas containing the mixture of methane and molecular oxygen, of the amount and of the enthalpy of the effluent and of the mixture containing the methane and the oxygen and of the effluent heat capacity. In the case of a reactor (5) of the circulating or fluidized bed type, the mixture of methane and of molecular oxygen is introduced into the bottom of said reactor (5); this charge then draws the hot contact mass which is driven to the top of reactor (5); then, this contact mass can generally either go down to the bottom of reactor (5), by a different way, where it is drawn again, or be transferred outside reactor (5) for a further treatment before being drawn again.

A flow (7) of an ethane-rich gas is then added to the effluent of reactor (5), in a place where at least about 80% (preferably at least about 95%) of the molecular oxygen have been consumed.

Said ethane-rich added gas (7) can be introduced at room temperature or pre-heated at a temperature lower than the effluent temperature. In both cases, said added gas (7) is used for lowering the effluent temperature and it produces then a mixture which is at a temperature that is lower than that of the effluent. The temperature of the mixture can be controlled by adjusting the temperatures of the methane charge and of said added gas and the initial percentage of molecular oxygen. The residence time of the mixture (of the effluent and of said added gas) in pyrolysis reactor (8) is determined in relation to the mixture temperature and to the desired pyrolysis severity. The pyrolysis reaction can be carried out either in the absence of a contact mass or in the presence of a contact mass such as one of those which are known for the selective oxidation of methane.

A flow (9) of a propane-rich gas is then added to the effluent of reactor (8) in a place where said effluent has an olefins/$C_2+$ alkanes molar ratio of at least 0.5. This flow (9) to be added can be introduced at room temperature or pre-heated at a temperature lower than that of the effluent. In both cases, said added flow (9) is used for lowering the effluent temperature and it produces then a mixture which has a temperature that is lower than the effluent temperature. Said mixture goes through pyrolysis reactor (10) where its residence time is determined in relation to its temperature and to the desired pyrolysis severity. The pyrolysis reaction can be carried out either in the absence of a contact mass or in the presence of a contact mass such as those which are known for the selective oxidation of methane or such as those which are known for the dehydrogenation of propane.

The effluent gas of reactor (10) is quenched (11) and carried off (12) if it is going to be used as it is. It is also possible to recycle it (13); it is then often advantageous to subject said gas to various treatments such as:

drain, which allows one to avoid an accumulation of gases such as $H_2$, He, $N_2$ or CO:

amine washing, allowing one to remove $CO_2$;

methanation, allowing one to convert CO and $H_2$ into $CH_4$ and $H_2O$.

These treatments are globally represented by unit (14); the separated gases are removed through line (15). The remaining gas, which comprises non converted hydrocarbons, ethylene and propene, is fed into separator (1) through line (16).

The $C_2+$ hydrocarbons coming from separator (1) through line (14) are subjected to various treatments such as, for example:

fractionating by condensation under pressure at low temperature, allowing the separation of the $C_2$, $C_3$ and $C_4+$ fractions;

absorption in sulfuric acid, oligomerization of the olefins into liquid fuels (for example into gasoline and/or gas oil) or dimerization reaction allowing the separation of the olefins from the $C_2$, $C_3$ and $C_4+$ alkanes; and/or any combination of methods known by the man skilled in the art and allowing the separation of olefins from $C_2$, $C_3$ and $C_4+$ alkanes.

These treatments are globally represented by units (17) and (20). The gas fraction rich in $C_2+$ hydrocarbons from separator (1) is fed into separator (17) through line (4): a gas fraction rich in propane is separated in unit (17) and fed towards pyrolysis reactor (10) through line (9); a gas fraction rich in unsaturated $C_3$ and in $C_4+$ hydrocarbons is discharged from unit (17) through pipe (18); a gas fraction rich in $C_2$ hydrocarbons is separated in unit (17) and fed into separator (20), through line (19), where an ethane-rich gas fraction is separated from an ethylene-rich gas fraction. The ethane-rich gas fraction is then transferred to pyrolysis reactor (8) through line (7); the ethylene-rich gas fraction is discharged from unit (20) through pipe (18).

Lines (22) and (23) allow one to take samples, especially in order to measure the conversion of the molecular oxygen and the olefins/$C_2+$ alkanes molar ratio.

Whatever the type of the reactors used in the process according to the invention, it is possible to utilize distinct reaction sections for stages (2), (5) and (7) of said process (FIG. 1) or only one section comprising three successive reaction zones (FIG. 2).

What is claimed is:

1. A process for producing olefins from natural gas containing methane, ethane and propane, comprising:
   (1) separating the natural gas into two fractions, a first gas fraction enriched in methane and a second gas fraction enriched in hydrocarbons higher than methane,
   (2) selectively oxidizing the first gas fraction enriched in methane with molecular oxygen, in the presence of a contact mass, to form an effluent containing $C_2$ hydrocarbons and water as products,
   (3) separating the second gas fraction enriched with hydrocarbons higher than methane into two new fractions, a first gas fraction enriched in propane and a second gas fraction enriched in ethane,
   (4) admixing the second ethane-enriched gas fraction from stage (3) with the effluent from stage (2) after at least about 80% by volume of the molecular oxygen has been consumed in stage (2),
   (5) pyrolyzing the mixture resulting from stage (4) to form an olefins/$C_2+$ alkanes ratio of at least 0.5,
   (6) admixing the first propane-enriched gas fraction from stage (3) with the effluent from stage (5), and
   (7) pyrolyzing the mixture resulting from stage (6) to form an olefin-rich gaseous mixture.

2. A process according to claim 1 wherein the second gas fraction enriched with ethane and stemming from stage (3) is admixed, prior to stage (4), with a gas enriched in ethane which does not stem from the natural gas.

3. A process according to claim 1 the first gas fraction enriched with propane and stemming from stage (3) is admixed, prior to stage (6), with a gas enriched with propane which does not stem from the natural gas.

4. A process according to claim 1, in stage (2), the oxygen proportion ranges from about 0.001 to 0.4 mole per mole of methane.

5. A process according to claim 1 wherein the mixture of stage (4) is carried out when at least 95% by volume of the molecular oxygen have already been consumed in stage (2).

6. A process according to claim 1 wherein stages (2), (5) and (7) are carried out at a temperature ranging from about 650° to about 1,200° C. and under a pressure ranging from about 1 to about 100 bars.

7. A process according to claim 1 wherein the contact mass of stage (2) is the following formula: $T_aLn_2O_b\text{-}{}_c(CO_3)_c$, where T represents at least one alkaline-earth metal, Ln represents at least one rare-earth metal, $a=0.001$ to $1,000$; $b=3+a$; $c=0.1$ to $b$.

8. A process according to claim 1 wherein the contact mass of stage (2) answers the following formula: $T_a\text{-}M_dLn_2O_e\text{-}{}_f(CO_3)_f$, where T represents at least one alkaline-earth metal, Ln represents at least one rare-earth metal. M represents one or several metals from group IV A, $a=0.001$ to $1,000$; $d=0.001$ to $2$; $e=3+a+2d-z$; $f=0.1$ to $e$; and $z=0$ to $0.5d$.

9. A process according to claim 1, wherein the effluent from stage (7) is fractionated; the carbon dioxide is removed, carbon monoxide is subjected to methanation in order to convert CO and $H_2$ into $CH_4$ and $H_2O$, and resulting gaseous effluent, containing non-converted hydrocarbons, ethylene, and propene, is fed back to stage (1).

10. A process according to claim 1 for producing ethylene and propene.

11. A process according to claim 2, wherein the first gas fraction enriched with propane and stemming from stage (3) is admixed prior to stage (6) with a gas enriched with propane which does not stem from the natural gas.

12. A process according to claim 2, wherein the effluent from stage (7) is fractionated; the carbon dioxide is removed, carbon monoxide is subjected to methanation in order to convert CO and $H_2$ into $CH_4$ and $H_2O$, and resulting gaseous effluent, containing non-converted hydrocarbons, ethylene, and propene, is fed back to stage (1).

13. A process according to claim 3, wherein the effluent from stage (7) is fractionated; the carbon dioxide is removed, carbon monoxide is subjected to methanation in order to convert CO and $H_2$ into $CH_4$ and $H_2O$, and resulting gaseous effluent, containing non-converted hydrocarbons, ethylene, and propene, is fed back to stage (1).

14. A process according to claim 11, wherein the effluent from stage (7) is fractionated; the carbon dioxide is removed, carbon monoxide is subjected to methanation in order to convert CO and $H_2$ into $CH_4$ and $H_2O$, and resulting gaseous effluent, containing non-converted hydrocarbons, ethylene, and propene, is fed back to stage (1).

15. A process according to claim 14, wherein the mixture of stage (4) is carried out when at least 95% by volume of the molecular oxygen have already been consumed in stage (2).

16. A process according to claim 4, wherein stages (2), (5), and (7) are carried out a temperature ranging from about 650° to about 1200° C. and under a pressure ranging from about 1 to about 100 bars.

17. A process according to claim 5, wherein stages (2), (5), and (7) are carried out a temperature ranging from about 650° to about 1200° C. and under a pressure ranging from about 1 to about 100 bars.

18. A process according to claim 11, wherein stages (2), (5), and (7) are carried out a temperature ranging from about 650° to about 1200° C. and under a pressure ranging from about 1 to about 100 bars.

19. A process according to claim 14, wherein stages (2), (5), and (7) are carried out a temperature ranging from about 650° to about 1200° C. and under a pressure ranging from about 1 to about 100 bars.

20. A process according to claim 15, wherein stages (2), (5), and (7) are carried out a temperature ranging from about 650° to about 1200° C. and under a pressure ranging from about 1 to about 100 bars.

21. A process for producing olefins from natural gas containing methane, ethane and propane, comprising:
    (1) separating the natural gas into two fractions, a first gas fraction enriched in methane and a second gas fraction enriched in hydrocarbons higher than methane,
    (2) selectively oxidizing the first gas fraction enriched in methane with molecular oxygen, in the presence of a contact mass, to form an effluent containing $C_2$ hydrocarbons and water as products,
    (3) separating the second gas fraction enriched with hydrocarbons higher than methane into two new fractions, a first gas fraction enriched in propane and a second gas fraction enriched in ethane, and
    (4) admixing the second ethane-enriched gas fraction from stage (3) with the effluent from stage (2) after at least about 80% by volume of the molecular oxygen has been consumed in stage (2).

22. A process according to claim 21, further comprising pyrolyzing the mixture resulting from stage (4) in stage (5) to form an olefins/$C_2+$ alkanes ratio of at least 0.5.

23. A process according to claim 22, further comprising admixing the first propane-enriched gas fraction from stage (3) with the effluent from stage (5).

* * * * *